(12) United States Patent
Quist et al.

(10) Patent No.: US 6,519,033 B1
(45) Date of Patent: Feb. 11, 2003

(54) IDENTIFICATION OF PARTICLES IN FLUID

(75) Inventors: Gregory M. Quist, Escondido, CA (US); Hanno Ix, Escondido, CA (US)

(73) Assignee: Point Source Technologies, LLC, Escondido, CA (US)

( * ) Notice: Subject to any disclaimer, the term of this patent is extended or adjusted under 35 U.S.C. 154(b) by 0 days.

(21) Appl. No.: 09/988,482

(22) Filed: Nov. 19, 2001

(51) Int. Cl.[7] .............................................. G01N 21/00
(52) U.S. Cl. ...................................... 356/337; 356/338
(58) Field of Search ................................ 356/337, 338, 356/343, 335

(56) References Cited

U.S. PATENT DOCUMENTS

| | | | |
|---|---|---|---|
| 3,770,351 A | 11/1973 | Wyatt | |
| 3,901,602 A | 8/1975 | Gravatt, Jr. | |
| 4,070,113 A | 1/1978 | Frazer et al. | |
| 4,173,415 A | 11/1979 | Wyatt | |
| 4,265,538 A | 5/1981 | Wertheimer | |
| 4,548,500 A | 10/1985 | Wyatt | |
| 4,565,448 A | 1/1986 | Abbott et al. | |
| 4,661,913 A | * 4/1987 | Wu et al. | 364/500 |
| 4,728,190 A | 3/1988 | Knollenberg | |
| 4,906,094 A | 3/1990 | Ashida | |
| 4,942,305 A | 7/1990 | Sommer | |
| 4,952,055 A | 8/1990 | Wyatt | |
| 4,987,539 A | 1/1991 | Moore et al. | |
| 5,125,737 A | 6/1992 | Rodriguez et al. | |
| 5,247,340 A | 9/1993 | Ogino | |
| 5,414,508 A | 5/1995 | Takahashi et al. | |
| 5,436,465 A | 7/1995 | Borden et al. | |
| 5,469,369 A | * 11/1995 | Rose-Pehrsson et al. | 364/497 |
| 5,534,999 A | 7/1996 | Koshizuka et al. | |
| 5,627,040 A | 5/1997 | Bierre et al. | |
| 5,737,078 A | 4/1998 | Takarada et al. | |
| 5,999,256 A | 12/1999 | Jones et al. | |
| 6,023,324 A | 2/2000 | Myers | |
| 6,100,541 A | 8/2000 | Nagle et al. | |
| 6,118,531 A | 9/2000 | Hertel et al. | |
| 6,120,734 A | 9/2000 | Lackie | |
| 6,421,121 B1 | * 7/2002 | Haavig et al. | 356/338 |

FOREIGN PATENT DOCUMENTS

GB 2317228 A 3/1998

OTHER PUBLICATIONS

"Discrimination of phytoplankton via light-scattering properties" By: Philip J. Wyatt and Christian Jackson, Year 1989, pp. 96–112.

* cited by examiner

Primary Examiner—Frank G. Font
Assistant Examiner—Layla Lauchman
(74) Attorney, Agent, or Firm—Leon D. Rosen

(57) ABSTRACT

A method for the identification of unknown microscopic particles in a fluid. A laser beam (104) is directed through the fluid while particles move through the beam. Light scattered by each particle moving through a short detect zone (114) along the beam (an "event") is detected by some of sixteen detectors DA–DP to generate data for the event. First, a known specie of particles (e.g. a particular pathogen specie) is placed in pure fluid and a subpattern, or eventvector, of data is recorded for each of multiple events for that specie. Each eventvector represents the outputs of all detectors. The process is repeated for other known species (e.g. algae) likely to be encountered. The group of eventvectors for all selected species is analyzed by an algorithm that determines a projection direction that results in the closest grouping of eventvectors of the same specie and greatest of separation of groups of eventvectors of different species. When an unknown particle is detected and produces an unknown particle eventvector, the program views the eventvector from the previously determined projection direction, to determine whether or not the unknown particle eventvector falls into one of the groups of known eventvectors so the particle can be identified as one of the known species or not.

9 Claims, 4 Drawing Sheets

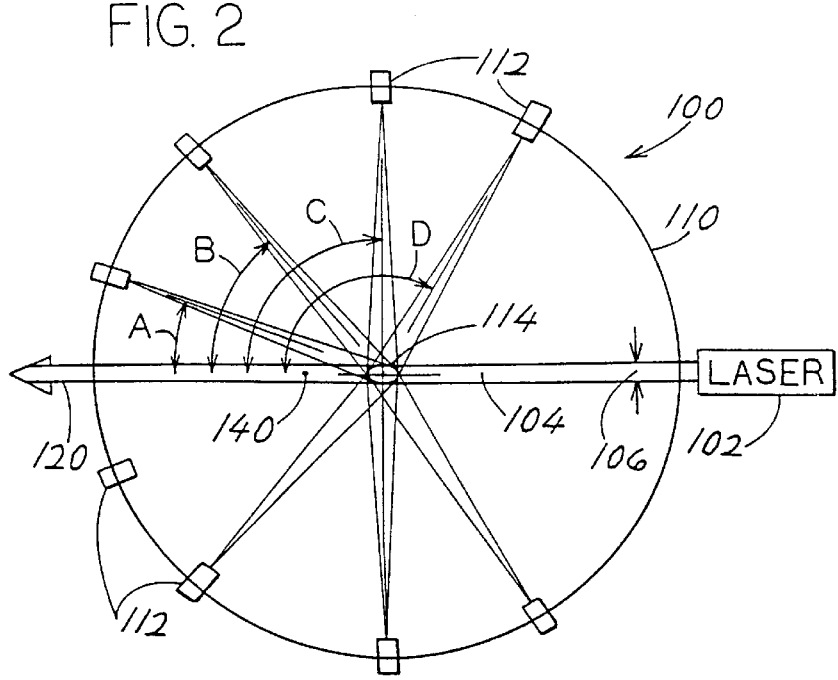
FIG. 2
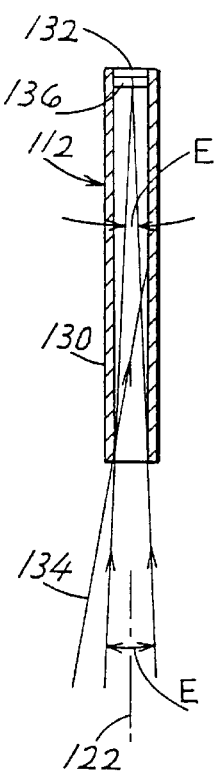
FIG. 3
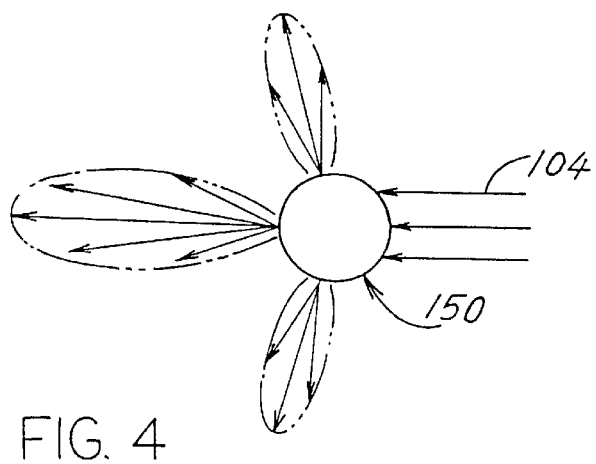
FIG. 4
FIG. 5

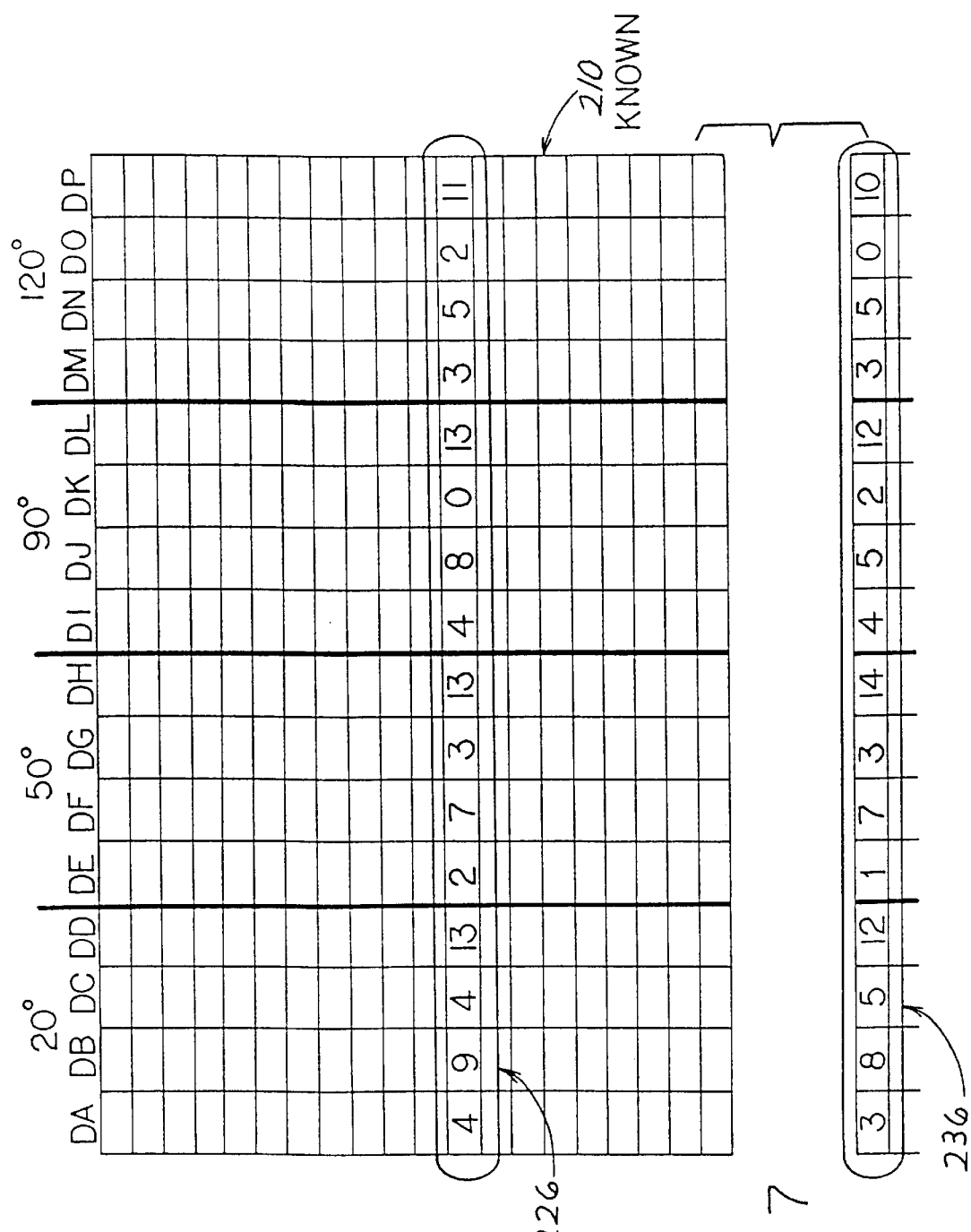

IDENTIFICATION OF PARTICLES IN FLUID

BACKGROUND OF THE INVENTION

There is a need to detect and identify unknown microscopic particles (e.g. no more than about 25 microns diameter) such as pathogenic microorganisms in fluid such as water or air. Protozoan parasites such as *Cryptosporidium parvum*, and *Giardia lamblia* are involved in water born outbreaks of disease, as they are present in the effluent of even state-of-the-art water treatment plants complying with current regulations. Current water quality monitoring techniques can take at least a day for results, are labor intensive and expensive, and have an unacceptably poor accuracy of identification. These monitoring techniques include immuno-fluorescence assay (IFA) and flow cytometry cell sorting (FCCS), as well as new techniques such as DNA Microarrays.

Attempts to monitor water for the presence and identity of microorganisms by optical techniques has met with mixed success. Although the presence of particles is readily detected by these techniques, it is difficult to identify the particles. In a technique in which one of the present inventors was an inventor, described in U.S. Pat. No. 4,548,500, microscopic particles of regular geometric shape were identified. That technique called Multi-Angle Light Scattering (MALS) used an approach called "strip maps." Simple particles such as homogeneous and isotropic spheres, homogeneous rods, and homogeneous ellipsoids were identified using optical data generated solely from the differential cross section (the angular dependence of the scattering amplitude). However, the strip map technique is limited to simple geometric structures.

In another test (described in an article by P. G. Wyatt and C. Jackson, Limnology and Oceanography, January 1989, pp. 96–112) detectors all lying in one plane were used to detect light scatter from twelve different species of phytoplankton in water. The scientists observed that the light scatter patterns for the difference species appear to be generally different. However, no way was known for using this data to identify an unknown particle as being a particular one of the twelve species or not any one of those species.

Although the identification of microorganisms in water is especially useful, it is also useful to be able to identify microorganisms in air, which may be pathogens spread by accident or deliberately by terrorists.

SUMMARY OF THE INVENTION

In accordance with one embodiment of the present invention, a method and apparatus are provided for the identification of unknown microscopic particles contained in a fluid such as water. The apparatus includes a source for generating a beam of energy such as a light beam from a laser. Fluid that contains particles is flowed through a detect zone lying along the laser beam. A plurality of detectors detect light scattered or otherwise dispersed (diffracted, refracted and transmitted) by a particle to the multiple locations of the detectors. A particle passing through the detect zone is an "event". The outputs of the multiple detectors, as a result of an unknown particle passing through the detect zone, represent an unknown subpattern, or eventvector. The unknown eventvector is compared with the multiple eventvectors obtained by detecting particles of a number of known species. If the eventvector for the unknown particle fits into one of the groups of eventvectors of a known specie of particle, then the unknown particle is deemed to be that specie of known particle.

A first step is to obtain multiple light scatter eventvectors for particles that are all of the same known specie. This is repeated for several different known species. The eventvectors are then analyzed using an algorithm that clusters the eventvectors, so as to group all eventvectors representing particles of the same specie as closely as possible, while separating groups of eventvectors representing particles of different species as far apart as possible. When an unknown particle is detected, its eventvector is compared to the eventvectors of those of a known specie. If the eventvector for the unknown particle lies within a volume that contains all retained eventvectors of a known specie of particles or lies is within a certain distance of the group of eventvectors of a known specie of particle, then the unknown particle is deemed to belong to that known particle class. Otherwise, the unknown particle cannot be identified.

Applicant prefers to use the MANOVA (Multiple Analysis of Variance) technique that analyzes data with a computer program that performs the above process.

The novel features of the invention are set forth with particularity in the appended claims. The invention will be best understood from the following description when read in conjunction with the accompanying drawings.

BRIEF DESCRIPTION OF THE DRAWINGS

FIG. 2 is a simplified view of the detector system of the arrangement of FIG. 1.

FIG. 3 is a sectional view of a detector of the system of FIG. 2.

FIG. 4 depicts the interrogation of a spherical particle.

FIG. 5 depicts the interrogation of a "pear" shaped particle with an inclusion.

FIG. 7 depicts eventvectors obtained from the interrogation of a known particle and an unknown particle.

DESCRIPTION OF THE PREFERRED EMBODIMENTS

Figure 1:
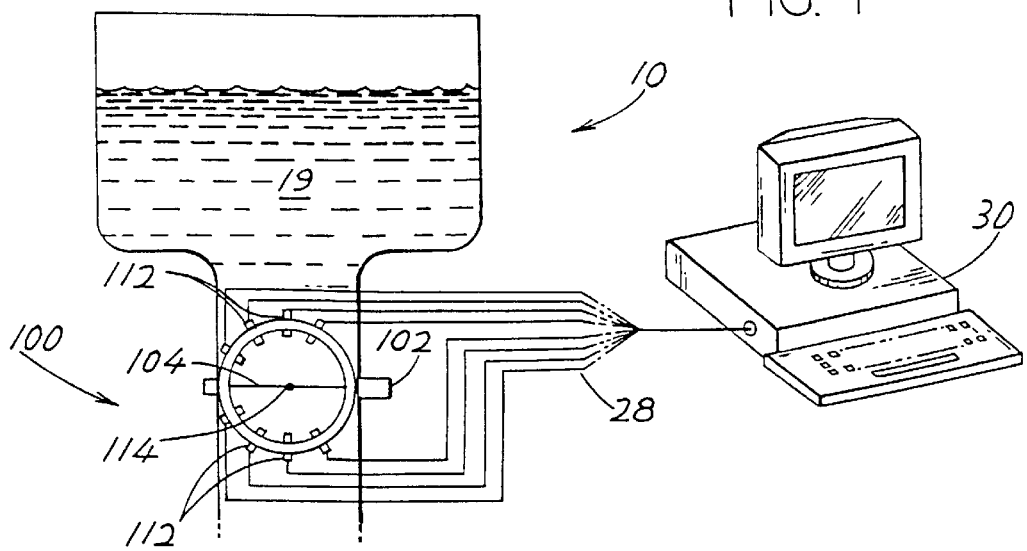
FIG. 1 is a schematic block diagram showing the major components of one embodiment of a particle identifying arrangement of the present invention.

FIG. 1 is a largely schematic block diagram of an arrangement 10 for identifying particles in a sample 19 of water. The sample may, for example, be taken from a reservoir that supplies drinking water. The system includes a detector system or apparatus 100 that includes a laser 102 that generates a laser beam 104 that passes through the water. Multiple detectors 112 detect light dispersed (scattered, reflected, refracted, emitted, etc.) from a detect zone 114 lying along the laser beam. In the following discussion, applicant will sometime use the term "scatter" to indicate all processes by which light is diverted from the straight line of the laser beam by a particle, or by which the energy of light causes the particle to emit light. The output of all detectors 112 is delivered through a cable 28 to a computer 30. The computer contains a program that analyzes data from the detectors to enable the identification of an unknown particle.

FIG. 2 illustrates more details of the system 100 for identifying particles. The laser 102 generates a thin collimated laser beam 104. Applicant generally prefers to use light in a range of wavelengths between and including infrared to far ultraviolet, and possibly even to soft x-rays. The particular beam 104 is vertically polarized light having a wavelength of approximately 685 nm which is red light. The microorganism particle to be detected will have a diameter in the range of about one to thirty wave-lengths (about one to 20 microns). The beam is narrow, having a width of perhaps 1.5 mm (0.060 inch) and a height or thickness of 0.1 mm (0.004 inch). A detector support 110 supports a plurality of detectors 112, with each detector oriented to detect light emitted from a short detect zone 114 lying along the laser beam 104. Each detector 112 is spaced about 60 mm from the detect zone. The detectors are located at different angles a–D from the forward direction of travel of the laser beam 104.

FIG. 3 shows one of the detectors 112, showing how it detects light received through a narrow angle E such as 1.5° from the direction 122 in which the detector is aimed. The detector includes an elongated narrow tube 130 with an inside surface that absorbs red light. A photocell element 132 lies at the distal end of the tube. Light traveling along a path indicated at 134, which is outside the narrow detection angle E, will strike the inside of the tube 130 and be absorbed there, so it will not be detected by the photodetector 132. Only light within the narrow angle E will be detected by the photocell element 132. It is also noted that a polarizing filter 136 lies over the photocell of the tube, to pass only light polarized in a certain direction, such as a vertical direction. A wide variety of types of detectors can be used, such as locations on a single piece of film, CCD's (charge coupled diode array), etc.

Referring again to FIG. 2, it can be seen that when a particle enters the detect zone 114, light from the laser beam 104 that encounters the particle will be scattered, or dispersed from the particle. Some of that light may be detected by one or more of the detectors 112. A particle at a location such as 140 that is not in the detect zone 114, will disperse light, but such light will reach the detectors 112 only at large angles from their direction of viewing and will not be detected by the detectors.

FIG. 4 illustrates the type of dispersal of light from the laser beam 104 when it strikes a small transparent spherical article 150. It is noted that dispersion can change the polarization of light for non-spherical particles, and only those components of polarization that are parallel to the polarization of a detector filter will pass through it and be detected. The dispersion of light is largely Mie scattering, which occurs for particles that are about 2 to 100 times the wavelength of the light. The scattering pattern somewhat resembles the radio frequency output, with side lobes, of a common radio wave antenna.

FIG. 5 shows a particle 190 with a subregion 192 (e.g. a cell nucleus) embedded in the particle 190. The figure also shows a light scatter pattern which has additional lobes where the light amplitude is high.

In FIGS. 4 and 5 it is assumed that the particle diameter is about 2 to 100 times the light wavelength (about 1 to 50 microns diameter) so the dominant scattering is Mie scattering rather than conventional optical refraction and reflection. Actually, applicant attempts to identify particles of about 1 to 20 microns. Infrared and ultraviolet wavelengths can be used for greatly different particle sizes.

Figure 6:
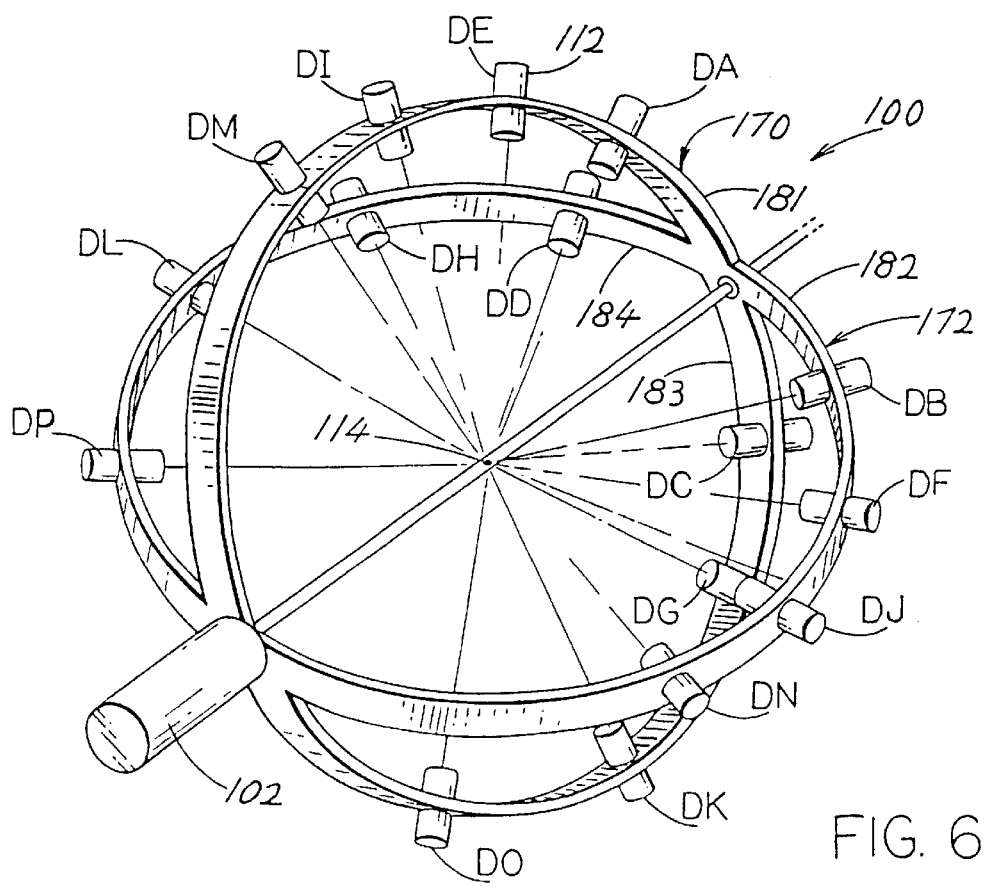
FIG. 6 is an isometric view of the system of FIG. 2.

FIG. 6 is an isometric view of the detection system 100 that includes rings 170, 172 lying on an imaginary sphere, and resulting in four quadrants 181–184. Sixteen detectors labeled DA–DP are provided, with four detectors in each quadrant. In one example, four detectors DA–DD in each of the four quadrants are spaced by an angle A (FIG. 2) of 20° from the beam direction 120, four others DE–DH are spaced by an angle B of 50°, four others DI-DL are spaced by an angle C of 90°, and four others DM–DP are spaced by an angle D of 120° from the forward direction 120.

In order to identify an unknown particle, applicant first creates an RSP (radiation scattering pattern) for one or more known species of particles, such as specific species of bacteria, that applicant wishes to detect and identify. For example, applicant might wish to detect a particular specie of pathogen, such as a protozoan that might be found in water that is be monitored. Applicant uses the term "specie" to mean very similar particles which are usually, but not always, classified as being of the same specie. Some species may be nonorganic particles such as microscopic bits of a particular material.

First a large number (perhaps millions) of the specie of pathogen particle to be identified is introduced to water that is otherwise free of all particles. Then, the water containing substantially only the known specie of particle (less than about 2% are not of that specie) is flowed past the laser beam of the apparatus of FIG. 6. Each time a particle passes through, or transits, the detect zone 114 of the laser beam, this results in light being detected by at least some of the detectors, and this is considered an event. The outputs of each of the sixteen detectors are considered to be a subpattern, or eventvector, and the eventvector, for each event is detected. In one example, perhaps one hundred particles are detected every minute passing through the detect zone.

The term "vector" in "eventvector" refers to the fact that an eventvector represents at least the paths of light scattered in each one of a plurality of directions, and preferably also the intensity of the light along each of the plurality of paths. This constitutes a set of vectors. The term "event" refers to the fact that the set of vectors in an eventvector relate to one event, which is when a particle (generally a single particle) passes through the detect zone.

In FIG. 7, one group 210 of boxes hold data that represents numerous detections or events of a known specie of particle, such as a pathogen. The group of boxes includes many rows, with each row containing sixteen boxes Da–DP that represent the outputs of each of the sixteen detectors (an eventvector) each time a particle is detected in the detect zone. Only about twenty rows are shown, but an analyzing circuit preferably contains many more (e.g. thousands). The eventvector stored in the row 226, plus the data in numerous other rows, provide the basis for an RSP (radiation scattering pattern) for that particular pathogen. Each row of sixteen outputs represents the light scattering (or other dispersion) characteristics for each of different variations of a specie (that vary slightly in size and shape) and for each of numerous different orientations with respect to the laser beam for each variation of the specie.

It should be noted that the outputs of each detector have a sensitivity range of 1 through about 64,000. In one example only approximate outputs are stored, with possible stored values ranging from $2^0$ through $2^{16}$ (1 through 64,000). The numbers in boxes 210 represent the number 2 with the exponent shown in the box.

Data such as shown in the rows of boxes 210 in FIG. 7, (which may include hundreds or thousands of rows similar to row 226) that each represent detector outputs for an event (an eventvector), are delivered to a computer that stores such data. Similar data representing events for one or more different known species, such as another pathogen or a type of algae expected to be found in water to be analyzed, is also delivered to the computer. The computer subjects all of this data to an algorithm such as MANOVA (multiple analysis of variance analysis) which is part of a program entitled Mat Lab offered by The Math Works located in Natick, Mass. The MANOVA algorithm or any similar algorithm, "views" or "projects" the data so as to enhance the separation of groups of eventvectors (there may be thousands of eventvectors in each group which represents an RSP) generated by particles of different species, while minimizing the separation of groups of eventvectors representing particles of the same specie. When an unknown particle is detected, its eventvector, represented in row 236, is compared to the groups of subpatterns of the known species.

Figure 8:
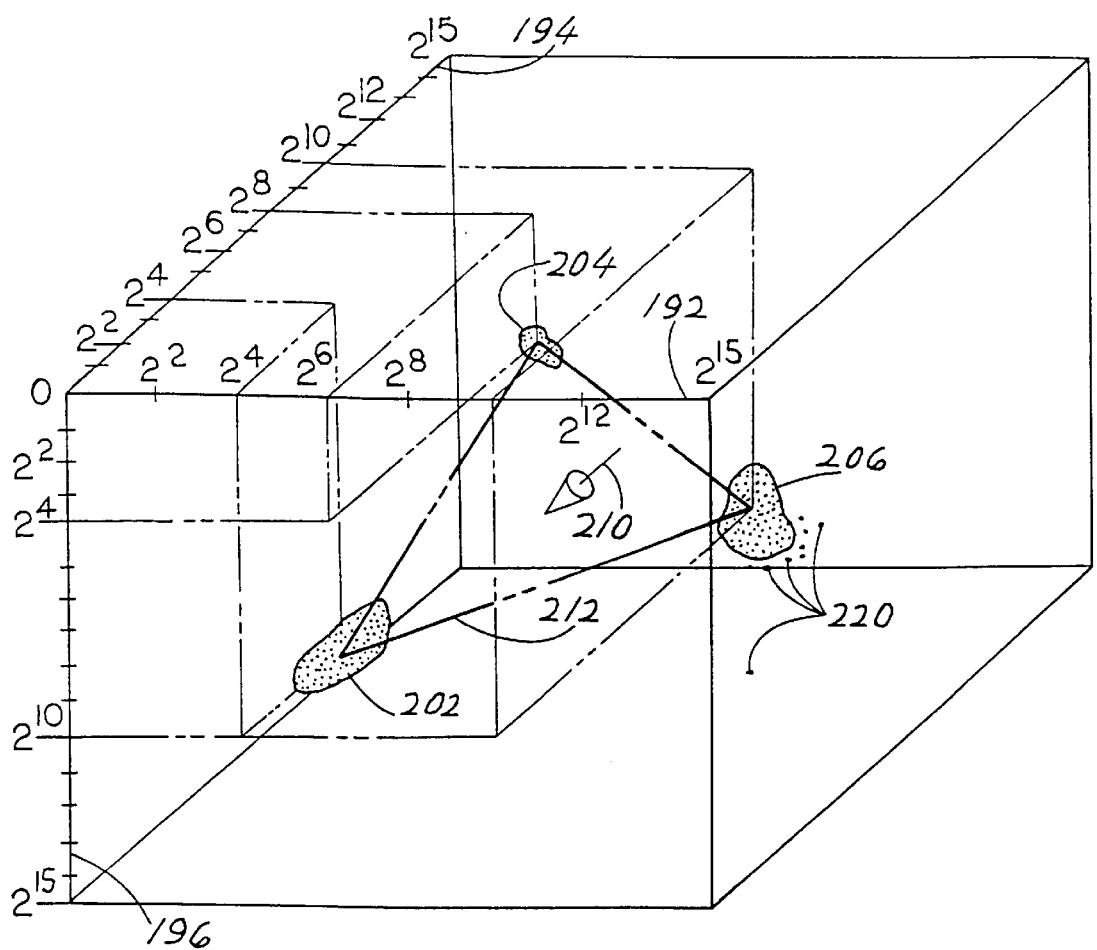
FIG. 8 is a simplified three dimensional representation of multi-dimensional analysis of the MANOVA analyzing technique of the arrangement of FIG. 1.

FIG. 8 is a simplified example, where only three detectors (instead of sixteen) have been used so the data representing the eventvectors (each comprising three numbers) can be arranged in three dimensions. The outputs of the detectors for an event determines the position of each point along each of three axes 192, 194,196. The output of each detector can range from $2^0$ (which equals one) through 216 (65,536). An output of noise or zero, is deemed to be 1. FIG. 8 shows the detector outputs for a first known specie lying in a space, or volume 202 and the detector outputs for second and third known species lying in volumes 204 and 206. The points in each volume, each represent one eventvector. Each volume represents the pattern for one specie of particles. In the example of FIG. 8, the center of volume 202 lies at the coordinates $2^4$, $2^4$, $2^{10}$ (16, 16, 1024). The center of volume 204 lies at 64 coordinates $2^6$, $2^8$, $2^4$, while the center of volume 206 lies at coordinates $2^{10}$, $2^{10}$, $2^{16}$.

The MANOVA technique might determine that the data is best viewed in the direction of arrow 210. Arrow 210 is normal to an imaginary plane 212 that connects the centers of the three volumes. The view along arrow 210 of the three volumes or patterns 202–206, results in the points (eventvectors) for each single specie (one volume) being closest together (minimum distance or variation), while the volumes occupied by the eventvectors of the three different species are furthest apart (greatest separation). Of course, a compromise must be made between the two criteria (minimum variation within group and maximum separation of different groups). It is noted that numerous points (eventvectors) such 220 deviate from the volume 206 for one specie while other points deviate from the other volumes. Data for these points such as 220 are discarded. Only points that fit close together in a small volume define the volume for one specie.

Figure 9:
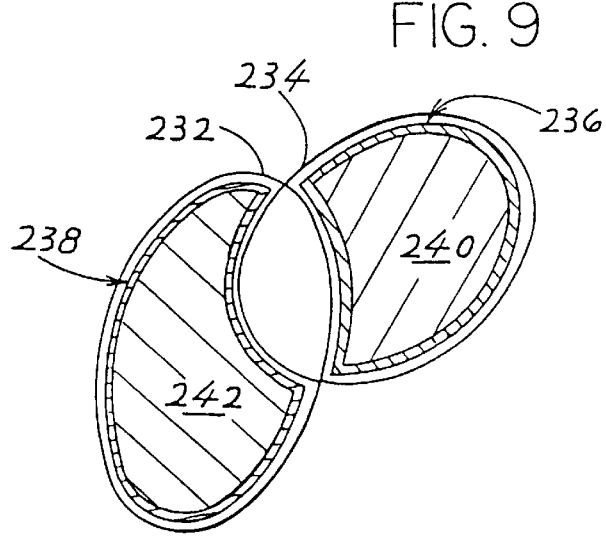
FIG. 9 is view of two groups of eventvector data points, showing how a Wall technique is applied to the MANOVA analysis.

It is also noted that in some situations, the data for the two (or more) species overlap. FIG. 9 shows two volumes 232, 234 of projected data that overlap when "viewed" or projected along the best projection direction (that produces minimum separation within any-specie and maximum separation between species). In that case, a "wall" 236, 238 is placed around the portion of each volume that does not overlap the other volume. The volumes 240, 242 for each known particle specie lies within the corresponding wall 236, 238. When an unknown particle is detected (by the three detectors), it is determined to be one of the known particles only if it falls into one of the known particle volumes 240, 242, when the eventvectors are viewed along the direction 210 of FIG. 8.

In actuality, there are more than three detectors, such as sixteen, and the MANOVA technique determines the best direction of viewing, or projection, when the eventvector data is arranged in more than the three dimensions of FIG. 8. Instead of using the power of two, the MANOVA technique often uses the logarithm of the detector, or photocell element outputs (to base 10 or e).

Instead of using the MANOVA program offered under the well-known software MatLab sold by The Math Works, any algorithm can be used that arranges data for minimum variance of data representing events for the same known specie, while achieving maximum separation of groups of data for different species. Examples of algorithms include MANOVA (multiple analysis of variances), neural networks, simulated annealing, algorithm-independent machine learning, fuzzy logic, grammatical methods, and various other techniques for pattern recognition. MANOVA and similar algorithms are used in the identification of people from fingerprints, voice, and facial appearance and other applications.

It may be noted that the intensity of the beam varies across the thickness of the beam, with greatest intensity at the center and falling off at greater distances from the center in a gaussian curve. Applicant prefers to use the maximum output of the detector, which is when the particle is at the center of the beam. It would be possible to take the integral of detector output during an event, a mean average value, etc. However, the particle undergoes negligible rotation during its brief passage (e.g. one millisecond) through the beam, so any of the values can be used.

While the invention has been described primarily for use in detecting pathogens in water, it also can be used to detect pathogens in air.

Thus, the invention provides a method and apparatus for identifying specific species of particles in a fluid, such as important pathogens in water and expected "background" particles species such as algae. The apparatus includes a plurality of detectors spaced about a detect zone, the detect zone lying along a beam of light (which may range from far ultraviolet light to infrared). In order to identify a particle as being one of a selected group of known species of particles, an RSP (radiation scattering pattern) is established for each known specie. This is accomplished by storing the outputs of the detectors (a subpattern, or eventvector) when a particle passes through the detect zone of the beam (an event) for each of numerous (e.g. thousands) of such events, where the particle for each event is of the same known specie of particle. In the usual case where more than one specie of particle (including background particles such as algae) are to be identified, the RSP for each of the other species is determined. The RSP's for all of the selected known species are delivered to a program such as the MANOVA program, which determines a "viewing" or projection direction in which the group of data points (eventvectors) for all events for particles of a single specie are close together, for each specie, while the groups of data points for the different species are separated far apart. When a fluid containing an unknown particles is to be analyzed, the fluid passes through the same or similar detection apparatus with multiple detectors. The data representing the outputs of all detectors for the event of that particular unknown particle (the eventvector), is then delivered to, the program which determines Whether the eventvector for the unknown particle event lies in one of the groups of subpatterns for one of the known particle species or is outside all of such groups. If the particle lies in a group, the particle is identified as of that specie. Otherwise, the particle is identified as unknown. If the particle is very close to a group representing a specie, this closeness can be indicated.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for identifying unknown particles that are present in a fluid, which includes interrogating particles by directing a beam of light along a beam direction through the fluid and detecting light scattered in a plurality of different directions that are angularly spaced from said beam direction by a plurality of detectors as a result of an event, which is when a particle passes through a detection zone that lies along said beam, and recording the outputs of said detectors for an event to produce an eventvector, comprising:

producing multiple events for particles that are of a known first specie, to produce multiple eventvectors for that known first specie, each eventvector for said known first species including a plurality of numbers that represent the outputs of a plurality of said detectors and at least the angular positions of said detectors;

producing an event for an unknown particle of an unknown specie to produce a eventvector for the unknown particle, said eventvector for said unknown particle including a plurality of numbers that represent the outputs of a plurality of said detectors;

comparing the multiple eventvectors for said known first specie to said eventvector for the unknown specie, to determine whether the unknown particle is of said known first specie.

2. The method described in claim 1 wherein said step of interrogating includes directing a beam of light through the fluid, and wherein:

said step of producing multiple events for particles of said known first specie includes placing multiple particles of said first specie in a first quantity of fluid that is originally substantially devoid of particles that would produce an eventvector, and conducting said step of interrogating for particles of said known first specie; and including producing multiple events for particles that are of a known second specie, to produce multiple eventvectors for that known second specie;

performing a comparison of the multiple eventvectors for said known first specie and the multiple eventvectors for said known second specie by an algorithm that groups the eventvectors of said first and second known species to produce first and second groups with largely maximum separation of said groups while producing largely minimum separation of eventvectors of the same group;

said step of comparing includes comparing the eventvector of said unknown particle to the eventvectors of said first and second groups of eventvectors to determine whether said eventvector of said unknown particle lies in one of said groups of eventvectors.

3. The method described in claim 2 wherein:

said step of performing a comparison includes comparing by the technique of Multiple Analysis Of Variances.

4. A method for identifying unknown particles that are present in a fluid, which includes interrogating particles by directing a beam of light through the fluid and detecting an event which occurs when a single particle transits a detection zone along said beam of light, said detecting of an event including detecting an eventvector representing at least the direction of light scattered by a particle during an event, as detected by each of a plurality of angularly spaced detectors, and recording said eventvectors that each represents the outputs of said detectors as a recording of a particle interrogation, including:

for each of a plurality of known species of particles, placing multiple particles of a selected one of said known specie of particle in a quantity of fluid to create a selected known quantity of fluid, and conducting said step of interrogating particles in said selected known quantity of fluid including recording the eventvector detected by said detectors, for each of a multiplicity of known-particle interrogations of said selected known particles of said selected known specie, where said multiplicity is more than 10, to create a selected known-particle pattern that includes a group of known eventvectors for each of said plurality of known species of particles;

conducting said step of interrogating, for an unknown quantity of fluid that contains at least one unknown specie of particle, including generating an eventvector of light detected by said detectors when an unknown particles is detected, to generate an unknown particle eventvector for the unknown particle where the unknown particle eventvector includes a plurality of numbers that each represents the output of a different one of said detectors that were positioned to detect light scattered in different directions, determining correlations of the plurality of numbers representing the unknown particle eventvector with each of said groups of known-particle eventvectors, and generating an output that indicates that the unknown particle is a first of said known species when the unknown particle eventvector of the unknown particle closely matches a first group of known eventvectors of a first of said known species of particles.

5. The method described in claim 4 wherein:

said step of determining correlations includes determining a largely optimum projection of said groups of known particle eventvectors in a multi-dimensional space to minimize the distance between eventvectors of the same group within the space and to maximize the distance between said groups, and said step of determining correlations includes determining whether or not the unknown particle eventvector lies in the space of one of said known groups.

6. The method described in claim 4 wherein:

said step of determining correlations includes analyzing said eventvectors by the technique of Multiple Analysis Of Variances.

7. The method described in claim 4 wherein:

said step of determining correlations includes grouping eventvectors for known particles of each of said plurality of known species of particles, into each of a plurality of multi-dimensional volumes;

in the event that two of said volumes would overlap if all eventvectors that fit into a group were included in that group, performing the step of eliminating from each volume that portion that would overlap the other volume, so no pair of volumes overlap.

8. Apparatus for identifying a specie of particle that is present in fluid that is to be analyzed, which includes means for generating a light beam and a plurality of detectors that each detects light scattered in a different direction from a detection zone lying along the beam when a particle enters the detection zone and thereby produces an event, the outputs of the detectors for an event constituting an eventvector for the event, comprising:

a memory that stores a plurality of known-particle patterns for particles of each of a plurality of known species, where each known-particle pattern comprises a group having multiple eventvectors that each includes a plurality of numbers representing the outputs of a plurality of detectors and the identity of the detectors, that were each recorded when a different particle of the same known specie of particle entered the detection zone to create an event;

pattern recognition means for indicating whether or not an unknown eventvector produced by an event of an unknown particle, wherein each eventvector includes a plurality of numbers that each represents the output of one of said detectors and that indicates the detector, is sufficiently similar to the eventvectors of one of said known-particle patterns to indicate that the unknown particle that produced the unknown subpattern is of one of said known species.

9. The apparatus described in claim 8 wherein:

said pattern recognition means is constructed to arrange each group of eventvectors in multiple dimensions and calculate an approximately optimum projection of the groups of known eventvectors where, along said optimum projection, the eventvectors of each group lies in a smallest space and the spaces of said groups are furthest apart, with said means being constructed to view said unknown eventvectors along said optimum projection to determine whether or not said unknown eventvector fits within a space of one of said known groups of eventvectors.

* * * * *